US012449198B2

(12) United States Patent
Tang et al.

(10) Patent No.: US 12,449,198 B2
(45) Date of Patent: Oct. 21, 2025

(54) TARGET RESIDUAL MOISTURE CONTENT FOR LYOPHILIZED DRUG PRODUCT

(71) Applicant: Regeneron Pharmaceuticals, Inc., Tarrytown, NY (US)

(72) Inventors: Xiaolin Tang, Old Tappan, NJ (US); Mary Kleppe, Milford, CT (US); Ravi Chari, Norwich, CT (US); Franco Tzul, Cortlandt Manor, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/755,396

(22) Filed: Jun. 26, 2024

(65) Prior Publication Data

US 2024/0393045 A1 Nov. 28, 2024

Related U.S. Application Data

(63) Continuation of application No. 18/208,018, filed on Jun. 9, 2023, now Pat. No. 12,066,246, which is a
(Continued)

(51) Int. Cl.
*F26B 5/06* (2006.01)
*A61K 9/19* (2006.01)

(52) U.S. Cl.
CPC . *F26B 5/06* (2013.01); *A61K 9/19* (2013.01)

(58) Field of Classification Search
CPC .................................. F26B 5/06; A61K 9/19
(Continued)

(56) References Cited

U.S. PATENT DOCUMENTS 5,336,616 A 8/1994 Livesey et al.
5,937,536 A * 8/1999 Kieselbach ............ F26B 5/044 34/92

(Continued)

FOREIGN PATENT DOCUMENTS

CN 101642565 A 2/2010
CN 108024535 A 5/2018

(Continued)

OTHER PUBLICATIONS

Wang Cuiyuan, Wu Rui, Yang Keli, Zhao Weiwei, Zhu Guangyi; Preparation and safety evaluation of a compound traditional Chinese medicine lyophilized powder; Journal of Traditional Chinese Veterinary Medicine, 01; Feb. 1, 2015.

(Continued)

*Primary Examiner* — Stephen M Gravini
(74) *Attorney, Agent, or Firm* — McCarter & English, LLP

(57) ABSTRACT

Lyophilization methods for preparing protein formulations for long-term storage at room temperature or improved stability at refrigeration storage are provided. Specifically, the present application provides lyophilization methods to obtain a target percentage of residual moisture of a lyophilized product, such as 3-5% residual moisture. The secondary drying of the lyophilization can be conducted under controlling rate of desorption under a temperature which is similar to the shelf temperature of the primary drying. Alternatively, the lyophilization can be conducted without a distinguished secondary drying step.

19 Claims, 8 Drawing Sheets

| Lyo Solution | % H2O at Offset |
|---|---|
| 5% Sucrose | 5 |
| 5% Mannitol | 4 |

Related U.S. Application Data continuation of application No. 17/985,250, filed on Nov. 11, 2022, now Pat. No. 11,713,922, which is a continuation of application No. 17/167,527, filed on Feb. 4, 2021, now Pat. No. 11,525,629.

(60) Provisional application No. 62/969,961, filed on Feb. 4, 2020.

(58) Field of Classification Search
USPC .................................................... 34/284, 287
See application file for complete search history.

(56) References Cited

U.S. PATENT DOCUMENTS

| | | | | |
|---|---|---|---|---|
| 6,284,282 | B1 | 9/2001 | Maa et al. | |
| 7,572,893 | B2 | 8/2009 | Dix et al. | |
| 7,610,692 | B2 * | 11/2009 | Carin | F26B 23/022 34/388 |
| 8,240,065 | B2 | 8/2012 | Rampersad | |
| 8,407,912 | B2 * | 4/2013 | Hubbard, Jr. | F26B 3/12 424/159.1 |
| 8,795,669 | B2 | 8/2014 | Walsh et al. | |
| 9,193,801 | B2 | 11/2015 | Walsh et al. | |
| 9,453,676 | B2 * | 9/2016 | Robinson | C08L 5/00 |
| 9,863,699 | B2 | 1/2018 | Corbin, III et al. | |
| 10,113,797 | B2 | 10/2018 | Dern | |
| 10,472,425 | B2 | 11/2019 | Walsh et al. | |
| 10,813,988 | B2 | 10/2020 | Super | |
| 11,047,620 | B2 | 6/2021 | Beutler et al. | |
| 11,351,256 | B2 | 6/2022 | Tang et al. | |
| 11,377,505 | B2 | 7/2022 | Lim et al. | |
| 11,399,537 | B2 | 8/2022 | Xu | |
| 11,400,051 | B2 * | 8/2022 | Bronshtein | A61K 39/15 |
| 11,525,629 | B2 * | 12/2022 | Tang | F26B 5/06 |
| 11,660,333 | B2 * | 5/2023 | Dhere | C07K 14/18 424/204.1 |
| 11,674,751 | B2 * | 6/2023 | Deprez | F26B 5/06 34/60 |
| 11,713,922 | B2 * | 8/2023 | Tang | A61K 9/19 34/284 |
| 11,841,189 | B1 * | 12/2023 | Andrews | F26B 25/08 |
| 12,066,246 | B2 * | 8/2024 | Tang | F26B 5/06 |
| 2008/0172902 | A1 | 7/2008 | Gruber et al. | |
| 2008/0213215 | A1 | 9/2008 | Krishnan et al. | |
| 2010/0041870 | A1 | 2/2010 | Tchessalov et al. | |
| 2014/0259724 | A1 | 9/2014 | McCarthy et al. | |
| 2018/0099049 | A1 | 4/2018 | Tang et al. | |
| 2021/0239396 | A1 | 8/2021 | Tang et al. | |
| 2022/0031843 | A1 | 2/2022 | Cheng et al. | |
| 2022/0168353 | A1 | 6/2022 | Moskowitz et al. | |
| 2022/0241205 | A1 | 8/2022 | Stricwant et al. | |
| 2022/0265558 | A1 | 8/2022 | Bhambhani | |
| 2023/0263957 | A1 * | 8/2023 | Taha | C23C 16/505 |
| 2023/0358470 | A1 | 11/2023 | Tang | |
| 2024/0393045 | A1 * | 11/2024 | Tang | F26B 5/044 |

FOREIGN PATENT DOCUMENTS

| | | | | | |
|---|---|---|---|---|---|
| CN | 110022855 | A | | 7/2019 | |
| EP | 1870650 | A1 | * | 12/2007 | A61K 9/19 |
| EP | 2916090 | A1 | | 9/2015 | |
| JP | 2018-521078 | A | | 8/2018 | |
| WO | WO2006079722 | A2 | | 8/2006 | |
| WO | WO2013135826 | A1 | | 9/2013 | |
| WO | WO2015148444 | A1 | | 10/2015 | |
| WO | 2017/013169 | A1 | | 1/2017 | |
| WO | 2019/060115 | A1 | | 3/2019 | |
| WO | WO-2021021567 | A1 | * | 2/2021 | A61J 3/00 |

OTHER PUBLICATIONS

Wang Yan, Li Wei; Han Pinxin; Shu Yi; Liu Xia, Application of freeze-drying technology in injection of gemcitabine hydrochloride liposomes; Journal of Changzhou University (Nat Sci Ed), 01; Jan. 25, 2015.

International Search Report and Written Opinion for Application No. PCT/US2021/016569, dated Aug. 9, 2021, 20 pages.

* cited by examiner

| Lyo Solution | % $H_2O$ at Offset |
|---|---|
| 5% Sucrose | 5 |
| 5% Mannitol | 4 |

| Pure Excipient | Tg (°C) |
|---|---|
| Sucrose | 68-75 |
| MABB | NA |
| Arginine HCl | NA |
| PS80 | NA |
| Acetate | trace amount |
| Water | -140 |

TARGET RESIDUAL MOISTURE CONTENT FOR LYOPHILIZED DRUG PRODUCT

CROSS-REFERENCE TO RELATED APPLICATIONS

This application is a continuation of U.S. patent application Ser. No. 18/208,018, filed Jun. 9, 2023, which is a continuation of U.S. patent application Ser. No. 17/985,250, filed Nov. 11, 2022, now U.S. Pat. No. 11,713,922, which is a continuation of U.S. patent application Ser. No. 17/167,527, filed Feb. 4, 2021, now U.S. Pat. No. 11,525,629, which claims the benefit of U.S. Provisional Application No. 62/969,961, filed Feb. 4, 2020, which is herein incorporated by reference in its entirety.

FIELD OF THE INVENTION

The present application generally pertains to methods for lyophilization of protein formulations. Specifically, the present application provides lyophilization processes to obtain a target percentage of residual moisture of a lyophilized drug product which is stable for room temperature storage or has improved stability for refrigeration storage.

BACKGROUND

Most biopharmaceutical formulations are not stable in solution for long-term storage due to various forms of degradation, aggregation or chemical modification. Lyophilization, for example, freeze-drying under controlled conditions, is a preferred method to convert biopharmaceutical formulations, such as protein formulations, to a solid state to improve the product stability for long-term storage. The lyophilized product, for example, cake, is preferably stored at about 2-8° C. and/or at room temperature for a relatively long period of time. It also may be desirable that the cake has longer storage stability at room temperature to eliminate the requirement of refrigeration for the late phase protein drug during commercial transportation and storage around the world, especially in places where electricity and refrigeration may not be reliable.

Lyophilization is a relatively expensive process requiring a long processing time. Key objectives of optimizing lyophilization processes may include: optimizing the process without risking product collapse; determining the apparent end point of primary drying; and optimizing secondary drying to achieve desirable residual moisture content of the lyophilized products. Optimization of the freeze-drying cycle for a given biopharmaceutical formulation requires a balanced understanding of the lyophilization process, formulation characteristics, equipment capacities and practical risks associated with process parameters. (Chang et al., 2004, American Association of Pharmaceutical Scientists, pages 113-138, Freezing-drying process development for protein pharmaceuticals, Lyophilization of Biopharmaceuticals)

It will be appreciated that a need exists for methods of lyophilization which can generate lyophilized products having stabilities for long-term room temperature storage or has improved stability for refrigeration storage.

SUMMARY

Lyophilization is often a preferred method to convert biopharmaceutical formulations to a solid state for long-term storage. The lyophilized cake may be preferably stored at room temperature for a relatively long period of time. This application provides a lyophilization method to obtain a target percentage of residual moisture of a lyophilized product which has increased long term product stability for room temperature storage or has improved stability for refrigeration storage.

The conventional method of preparing a lyophilized cake comprises placing a formulation in a chamber of a freeze-dryer, such as placing the formulation in containers/vials on the shelves of the lyophilization chamber of the freeze-dryer; freezing the formulation, such as at low shelf temperature below −30° C.; conducting primary drying on the formulation to remove the frozen solvent molecule by sublimation, wherein the primary drying is conducted at a shelf temperature of the freeze-dryer that is relatively a low shelf temperature, for example, typically equal to or below about 0° C., under high vacuum, such as usually below 200 millitorr of a chamber pressure; and conducting secondary drying on the formulation to remove the desorbed solvent molecules to obtain a target weight percentage of the solvent molecule in the lyophilized cake, wherein the secondary drying is conducted at a relatively high shelf temperature at or above 25° C. under high vacuum, such as below 200 millitorr of chamber pressure.

This disclosure provides a method of preparing a lyophilized cake, comprising: preparing a formulation, wherein the formulation comprises at least one solvent molecule and a peptide or protein; subjecting the formulation to lyophilization to obtain the lyophilized cake including: (a) placing the formulation in a chamber of a freeze-dryer, such as placing the formulation in containers/vials on the shelves of the lyophilization chamber of the freeze-dryer, (b) freezing the formulation, (c) conducting first drying, for example, primary drying, on the formulation to remove the at least one frozen solvent molecule by sublimation, wherein the first drying is conducted at a shelf temperature of the freeze-dryer that is equal to or below about 0° C., and (d) conducting second drying, for example, secondary drying, on the formulation to remove the at least one solvent molecule to obtain a target weight percentage of the at least one solvent molecule in the lyophilized cake, wherein the second drying is conducted at the shelf temperature of the freeze-dryer that is equal to or below about 0° C. In some embodiments, there was no distinguished secondary drying. In some exemplary embodiments, the target weight percentage of the at least one solvent molecule in the lyophilized cake is about 3-5%, about 4% or about 4.5%.

In some exemplary embodiments, the at least one solvent molecule in the formulation is a water molecule. In some exemplary embodiments, the peptide or protein in the formulation of the present application is an antibody, an antibody fragment, a Fab region of an antibody, an antibody-drug conjugate, a fusion protein, a protein pharmaceutical product or a drug. In some exemplary embodiments, the lyophilized cake generated using the method of the present application is stable under the storage condition at room temperature or has improved stability for refrigeration storage.

In some aspects, the target weight percentage of the at least one solvent molecule in the lyophilized cake of the present application is controlled by the shelf temperature of the freeze-dryer for the second drying with a controlled drying rate. In some aspects, the target weight percentage of the at least one solvent molecule in the lyophilized cake of the present application is controlled by a duration time for the second drying.

In some aspects, the shelf temperature of the freeze-dryer of the second drying, for example, secondary drying, can be the same as the shelf temperature of the freeze-dryer of the first drying, for example, primary drying. In some aspects, the shelf temperature of the freeze-dryer of the second drying can be higher than the shelf temperature of the freeze-dryer of the first drying. In some aspects, the shelf temperature of the freeze-dryer of the second drying can be lower than the shelf temperature of the freeze-dryer of the first drying. In some aspects, the shelf temperature of the freeze-dryer for the second drying is equal to or slightly higher than the shelf temperature of the freeze-dryer for the first drying.

In some aspects, the method of the present application further comprises determining an ending of the first drying based on a change of a pressure in the chamber of the freeze-dryer. In some aspects, a temperature of the lyophilized cake is below a collapse temperature of the lyophilized cake in the first drying.

In some exemplary embodiments, the formulation of the present application further comprises a buffer, an excipient, a stabilizer, a cryo-protectant, a bulking agent, a plasticizer, or a combination thereof; wherein the stabilizer is polyol, sucrose, mannitol, trehalose, sorbitol, amino acid, or a combination thereof; wherein the cryo-protectant is surfactant, sugar, salt, amino acid, or a combination thereof. In some aspects, the buffer comprises acetate and/or histidine hydrochloride, the buffer has a pH value of about 5.3 or about 6, and the excipient is polysorbate 80. In some aspects, the stabilizer is sucrose, wherein the ratio of sucrose to the peptide or protein is about 1:1, about 3:1, about 10:1, or about from 1:1 to 10:1.

These, and other, aspects of the invention will be better appreciated and understood when considered in conjunction with the following description and the accompanying drawings. The following description, while indicating various embodiments and numerous specific details thereof, is given by way of illustration and not of limitation. Many substitutions, modifications, additions, or rearrangements may be made within the scope of the invention.

DETAILED DESCRIPTION

Figure 1:
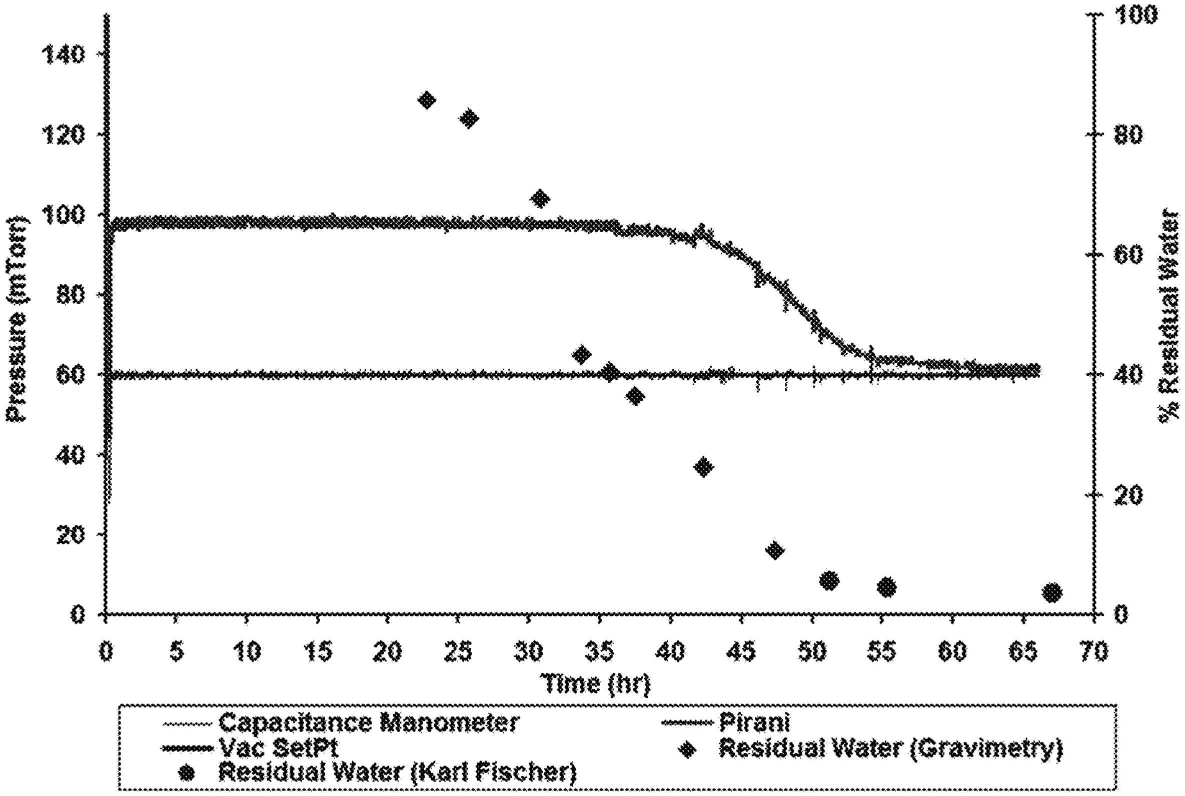
FIG. 1 shows the measurements of chamber pressures in lyophilization processes as indicated by Patel et al. Chamber pressure as measured by a capacitance manometer, chamber pressure as measured by the Pirani gauge and chamber pressure set point (Vac SetPt) were plotted against drying time according to Patel et al.

Lyophilization is a common method for preparing and manufacturing protein pharmaceuticals. Lyophilization, for example, freeze-drying, can be used to remove ice or other frozen solvents from a protein formulation through sublimation and to remove bound water molecules through desorption. There are various challenges in selecting critical process parameters to develop lyophilization processes. Conventional lyophilization of protein formulations can be carried out in three steps, for example, freezing, primary drying (sublimation) and secondary drying (desorption), such as freezing at about −45° C., primary drying at about −20° C. and secondary drying at higher temperature about 40° C., about 35° C.-55° C. or about 25° C.-55° C. The dried product of the protein formulation after the completion of primary drying can still have about 5-10% moisture content due to the presence of bound water molecules which are attached to the products. Conventional secondary drying is commonly conducted at much higher temperatures than those of the primary drying to reach less than about 1% or about 2% residual moisture content, such as drying at about 40° C., about 35° C.-55° C. or about 25° C.-55° C.

The present application provides a unique lyophilization process which is substantially different from conventional lyophilization processes. For example, the present application provides a unique lyophilization process by conducting a secondary drying at a controlling rate of desorption to achieve a target weight percentage of residual moisture at about 4.0%, about 4.5% or about 3-5%. The secondary drying of the present application can be considered as an extension of the primary drying, which can be conducted under a controlled rate of desorption at a temperature which is same as the shelf temperature of the primary drying, at a temperature which is slightly higher than the shelf temperature of the primary drying or at a temperature which is lower than the shelf temperature of the primary drying. In one aspect, the shelf temperature of the freeze-dryer for the second drying is equal to or slightly higher than the shelf temperature of the freeze-dryer for the first drying. Alternatively, the lyophilization can be conducted without a distinguished secondary drying step. The lyophilization of the present application is substantially different from the conventional lyophilization since the secondary drying of the present application can be conducted at a lower temperature which is substantially lower than the temperature of conducting conventional secondary drying.

There are various challenges in selecting critical process parameters to develop lyophilization processes, for example, conducting freezing, primary drying and secondary drying. Critical process parameters of lyophilization are primarily determined by the physicochemical characteristics of the product formulations, such as the collapse temperature and/or frozen state glass transition temperature (Tg') of the product formulation. The drying process can be well-controlled during the lyophilization process to avoid changes in the appearance and characteristics of the dried products by keeping the product temperature at favorable low temperatures during freezing and primary drying stage. For example, the drying processes including shelf temperature, chamber pressure, duration time and ramp rate of each process stage can be well-controlled during the lyophilization process. The present application provides processes to achieve a target moisture content in the lyophilized product by controlling the shelf temperature and duration for the secondary drying.

The freezing step of the lyophilization process includes freezing the product formulation to generate a solid matrix for drying. Sometimes, the freezing step may include an additional annealing step (Chang et al.) or a controlled nucleation step (Fang et al., Effect of Controlled Ice Nucleation on Stability of Lactate Dehydrogenase During Freeze-Drying, J Pharm Sci. 2018 March, 107(3):824-830). The primary drying step of the lyophilization process includes the removal of frozen solvent, such as ice, through sublimation by reducing the pressure while maintaining the product temperature at a low target level. The sublimation process refers to changes of a substance from solid phase (such as ice) to gas phase (such as vapor) directly without going through a liquid phase (such as water). Low pressures are generally required for the occurrence of sublimation. Sublimation, for example, an endothermic process, occurs at temperatures and pressures which are below a substance's triple point in the phase diagram corresponding to the lowest pressure at which the substance can exist as a liquid. In addition, since sublimation is an endothermic phase change, the addition of heat energy to the frozen substances is required that is provided by controlling the lyophilization shelf temperature above the product temperature during the primary drying. The product temperature is controlled to be several degrees below the collapse temperature (or Tg') by controlling both shelf temperature and chamber pressure. The secondary drying step of the lyophilization process includes the removal of bound water through desorption to reach desirable residual moisture content at a targeted level. During the drying process, the condenser is controlled at low temperature, for example, below −50° C.) and low pressure for effective transformation and trapping the sublimed solvent in the solid state.

The freeze-drying equipment can comprise a refrigeration system, a vacuum system, a control system, a product chamber and a condenser. The shelf temperatures of the product chamber of the freeze-dryer need to be controlled properly for conducting primary and secondary drying. During the primary drying step of the lyophilization process, the pressure of the chamber of the freeze-dryer can be reduced to lower than the saturated vapor pressure of frozen solvent at the frozen product temperature by introducing a vacuum. The primary drying step can be considered as reaching completion when all or substantially all frozen solvents are removed through sublimation. If there are bound unfrozen solvents remaining in the product formulation after the completion of the primary drying step, those can be removed by desorption at much higher temperatures during secondary drying for a conventional lyophilization process. (Chang et al.)

The apparent end point of primary drying (sublimation), for example, from the onset, midpoint and offset of the PG (Pirani gauge) chamber pressure, can be determined by various methods, such as comparative pressure measurement (Pirani gauge vs. capacitance manometer), dew point, gas plasma spectroscopy, water vapor concentration, condenser pressure, pressure rise test or product thermocouples (Patel et al., Determination of end point of primary drying in freeze-drying process control, AAPS PharmSciTech, Vol. 11, No. 1, March 2010). The Pirani gauge measures the thermal conductivity of the gas in the chamber. During lyophilization, chamber pressure can be controlled using a capacitance manometer which measures the absolute pressure in the chamber. The Pirani gauge reads about 60% higher than the capacitance manometer during primary drying when essentially all of the gas in the chamber is water vapor, since the thermal conductivity of water vapor is about 1.6 times of the thermal conductivity of nitrogen. When the Pirani pressure starts to sharply decrease, for example, the onset point, it indicates changes of gas composition from mostly water vapor to nitrogen, which can indicate the end of primary drying (Patel et al.). For example, changes of PG chamber pressure can be relevant to moisture content. Chamber pressure as measured by a capacitance manometer, chamber pressure as measured by the Pirani gauge and chamber pressure set points (Vac SetPt) are plotted against drying time as shown in FIG. 1 (according to FIG. 7 in Patel et al.). The percentages of residual moistures are measured by gravimetric and/or Karl Fischer methods.

Figure 2:
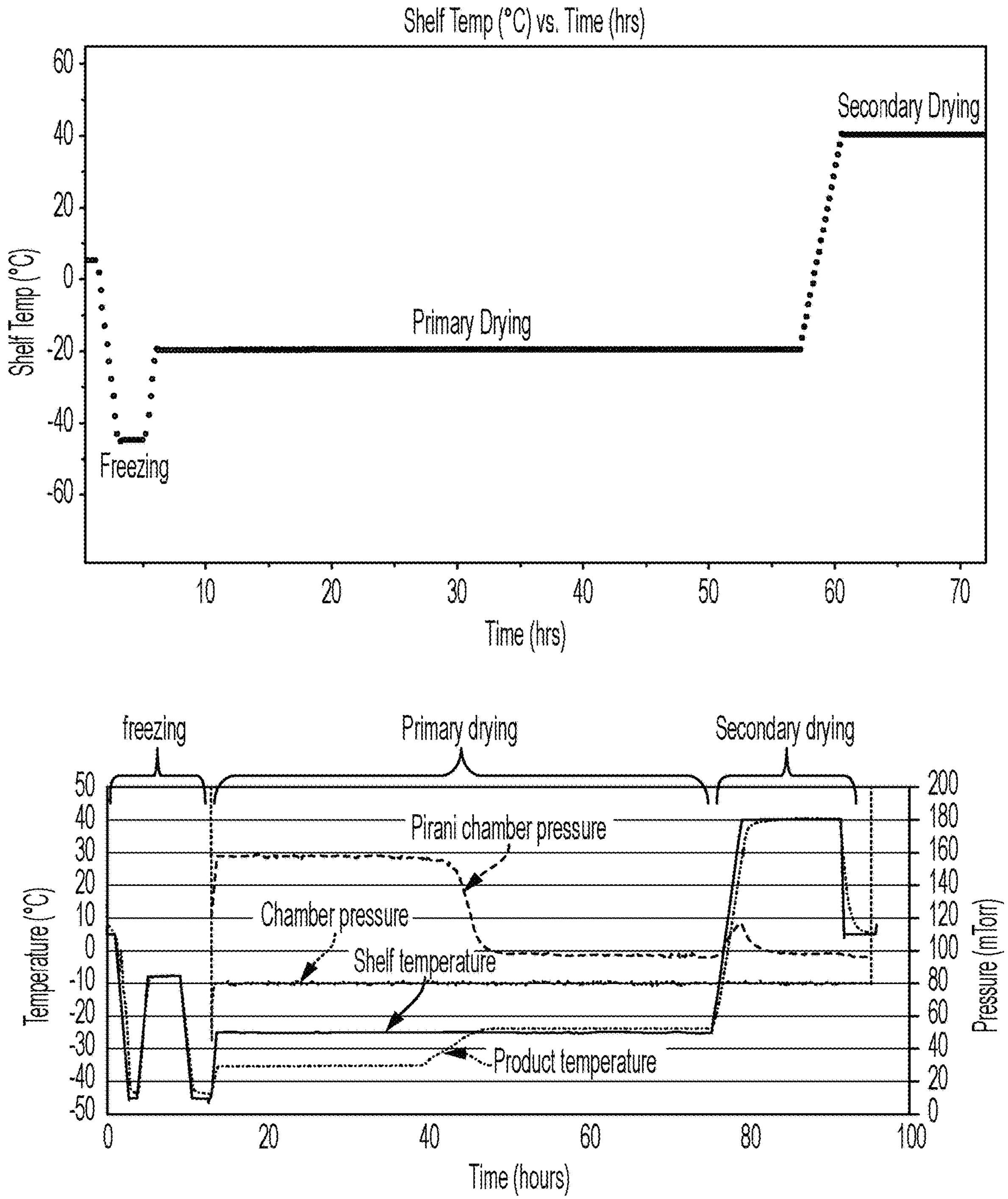
FIG. 2 shows conventional lyophilization processes including three steps, for example, freezing, primary drying and secondary drying. The conventional lyophilization is conducted at three steps including freezing at shelf temperature about −45° C., primary drying at shelf temperature about −20° C. or about −25° C. and secondary drying at higher temperature, such as at shelf temperature about 40° C. Conventionally, the secondary drying shelf temperature, such as at about 40° C., is always significantly above the primary drying shelf temperature, such as at about −20° C. or −25° C.

Commonly, lyophilization processes include three steps, for example, freezing, primary drying and secondary drying at higher temperature. For example, as shown in FIG. 2, the conventional lyophilization can be conducted at three steps including freezing at shelf temperature about −45° C. for about at least 120 minutes, primary drying at shelf temperature about −20° C. for about 1-3 days, and secondary drying at much higher temperature, such as about 40° C. In conventional lyophilization processes, bulk water can be removed by sublimation under a vacuum during primary drying at low temperature, such as in the range of from about −10° C. to about −35° C. of shelf temperature, or from about −40° C. to about −45° C. of shelf temperatures. During secondary drying, the bound unfrozen water remaining in the product can be removed by rapid desorption at high temperature, such as at about 40° C. of shelf temperature, as shown in FIG. 2. Commonly, the residual moisture content of the lyophilized product can reach less than about 1% by applying conventional secondary drying at high temperature. Typically, the residual moisture content of the lyophilized product can be reduced by increased shelf temperature and time duration of the secondary drying.

Figure 3:
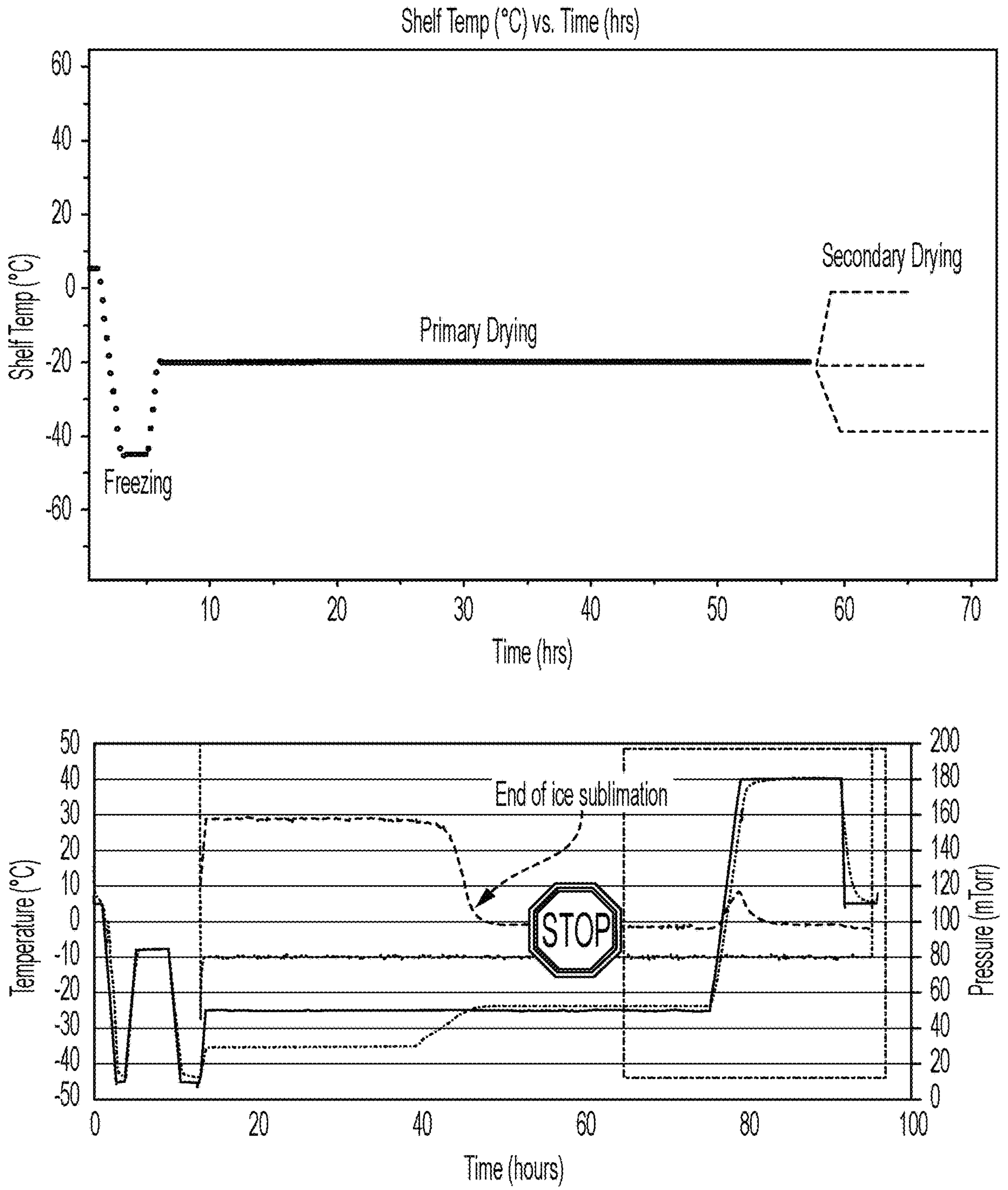
FIG. 3 shows a unique lyophilization process of the present application by conducting a secondary drying at controlling rate of desorption to achieve a target percentage of residual solvent according to an exemplary embodiment. Secondary drying of the present application is considered as an extension of the primary drying, which is conducted at: a low temperature, such as a temperature which is same as the shelf temperature of the primary drying; a temperature which is slightly higher than the shelf temperature of the primary drying; or a temperature which is lower than the shelf temperature of the primary drying; according to an exemplary embodiment. In some aspects, there is no distinguished secondary drying.

The present application provides a unique lyophilization process that is substantially different from the conventional lyophilization processes by conducting a secondary drying at controlled rate of desorption to achieve a target percentage of residual solvent. In some embodiments, there is no distinguished secondary drying. In some exemplary embodiments, the secondary drying of the lyophilization process of the present application can be conducted under controlled rate of desorption to achieve a target weight percentage of residual moisture of the lyophilized products, such as about 4.0%, about 4.5% or about 3-5%. In some aspects, the secondary drying of the lyophilization process of the present application can be conducted under controlled rate of desorption, wherein the shelf temperature of the secondary drying in the lyophilization process of the present application can be much lower than the shelf temperature of the conventional secondary drying. For example, secondary drying of the present application can be considered as an extension of the primary drying, which is conducted at low temperature, such as about −20° C., in the range of from about −10° C. to about −30° C., in the range of from about 0° C. to about −30° C., at a temperature which is same as the shelf temperature of the primary drying, at a temperature which is slightly higher than the shelf temperature of the primary drying or at a temperature which is slightly lower than the shelf temperature of the primary drying as shown in FIG. 3. In contrast, conventional secondary drying is conducted at high temperature, such as about 40° C. or in the range of from about 35° C. to about 55° C.

During primary drying, a sublimation front moves through the product to deposit dried product, for example, cake, above the ice surface interface and to sublime ice crystals. A desirable cake has mostly uniform appearance with some minor flaking or crumbling along the surfaces or edges. The dried product of the protein formulation after the completion of sublimation can have 5-10% moisture content due to the presence of bound water molecules which are attached to the products. In general, frozen products can be categorized as either crystalline or amorphous glass in structure. Glass transition temperatures (Tg') of the frozen product have been found to be strongly correlated with the collapse temperature (Tc) of the lyophilized cake during primary drying. The glass transition temperature can be considered as a temperature region where the dried product transitions from a rigid glassy state to a pliable rubbery state with higher mobility. The integrity of the cake structure can be maintained in glass state with negligible mobility when the product temperature is maintained below Tg'. It is important to maintain the product temperature during primary drying to be below Tg' of the protein formulation to prevent collapse of the cake. (Chang et al.) When cake becomes soft, the cake structure often cannot be maintained.

It is desirable that the cake has no sign of collapse or melt-back during freeze-drying. A desirable good cake possesses a rigid macroscopic structure and should not have collapse, discoloring and melt-back. The collapse (or partial collapse) of the cake can be due to the eutectic melting of crystalline agents in product formulation (at ice sublimation interface) during primary drying. It is desirable to keep the product temperature below the eutectic melting temperature of the crystalline components of the product formulation during primary drying. (Chang et al.) Melt-back of the cake can be considered as a form of partial or complete cake collapse caused by incomplete ice sublimation during primary drying. The product temperature is correlated to the vapor pressure at the ice sublimation interface. The vapor pressure is dependent on the rate of heat transfer into the product controlled by shelf temperature and the set point of the system vacuum level. The target product temperature can be maintained properly by controlling the shelf temperature and the system vacuum level (pressure) during primary drying.

In one embodiment, the process includes the steps of obtaining an aqueous sample containing a protein and an excipient in a container. The container can be a vial, a glass vial, a syringe barrel, or a chamber of a dual chamber auto-injector. The container can be sufficiently open to allow outgassing of water vapor. The container containing the aqueous sample is placed into a chamber and heat can be removed from the sample to attain a first temperature, wherein ice crystals form in the sample. Air can be removed from the chamber to attain a first pressure. Thermal energy can then be added to the sample to attain a second temperature to permit removal of the water from the sample by sublimation. Residual water may remain entrapped within the sample after sublimation, which can be removed through a second drying step. In one aspect, during the initial freezing and primary drying step, heat can be removed from the aqueous sample at a rate of about 0.5° C. per minute. In one aspect, the first temperature is about −45° C.

An excipient is an ingredient added alongside an active drug substance in a pharmaceutical formulation. Excipients can help to stabilize the drug substance and/or add bulk to the formulation. The term ingredient can be used interchangeably with excipients. Excipients include various substances for various purposes like buffering, bulking, solubilizing, stabilizing, plasticizing, and protecting the drug substance. Protectants can protect against thermal stress and/or physical stress like agitation. Cryoprotectants can protect protein from freezing stresses such as ice interface stress and freezing concentration stress. Lyoprotectants can protect protein from freezing and dehydration stresses. Excipients may include stabilizers. A stabilizer can be added to the pre-lyophilized solution to stabilize the protein against aggregation or other degradation. Stabilization may occur by controlling the glass dynamics during the lyophilization process or by helping to preserve the native structure of the protein through specific interaction of the stabilizer with the protein.

The needs of generating biopharmaceutical formulations which have stabilities for long-term storage at room temperature have led to an increasing demand for developing lyophilization processes. This disclosure provides methods to satisfy the aforementioned demands by providing methods for lyophilization of biopharmaceutical formulations to generate lyophilized products which have desirable characteristics and residual moisture contents.

Exemplary embodiments disclosed herein satisfy the aforementioned demands by providing lyophilization processes to obtain a target percentage of residual moisture of a lyophilized product which is stable for room temperature storage or has improved stability for refrigeration storage.

The term "a" should be understood to mean "at least one"; and the terms "about" and "approximately" should be understood to permit standard variation as would be understood by those of ordinary skill in the art; and where ranges are provided, endpoints are included.

As used herein, the terms "include," "includes," and "including," are meant to be non-limiting and are understood to mean "comprise," "comprises," and "comprising," respectively.

In some exemplary embodiments, this disclosure provides a method of preparing a lyophilized cake, comprising: preparing a formulation, wherein the formulation comprises at least one solvent molecule and a peptide or protein; subjecting the formulation to lyophilization to obtain the lyophilized cake, comprising: (a) placing the formulation in a chamber of a freeze-dryer, such as placing the formulation in containers/vials on the shelves of the lyophilization chamber of the freeze-dryer, (b) freezing the formulation, (c) conducting first drying (primary drying) on the formulation to remove the at least one frozen solvent molecule by sublimation, wherein the first drying is conducted at a shelf temperature of the freeze-dryer that is equal to or below 0° C., and (d) conducting second drying (secondary drying) on the formulation to remove the at least one solvent molecule to obtain a target weight percentage of the at least one solvent molecule in the lyophilized cake, wherein the second drying is conducted at the shelf temperature of the freeze-dryer that is equal to or below 0° C. Alternatively, the lyophilization can be conducted without a distinguished secondary drying step.

As used herein, the term "sublimation" refers to a phenomenon in lyophilization (freeze-drying) that water molecules (solvent molecules) pass directly from solid state (ice) to the vapor state without passing through the liquid state. During lyophilization, the product is frozen and placed under a vacuum, allowing ice to change directly from a solid state to a vapor state without passing through a liquid state. Sublimation is an endothermic process which occurs at temperatures and pressures which are below a substance's triple point in the phase diagram corresponding to the lowest pressure at which the substance can exist as a liquid. Sublimation of water can take place at pressures and temperatures below triple point, for example, 4.579 mmHg and 0.0099° C. The rate of sublimation of ice from a frozen product depends upon the difference in vapor pressure of the product at ice sublimation interface compared to the vapor pressure of the lyophilization chamber which is usually slightly above or equal to the pressure of the cold trap (Nireesha et al., Lyophilization/freeze drying-an review, International Journal of Novel Trends in Pharmaceutical Sciences, page 87-98, volume 3, No. 4, October 2013; Chang et al.). The rate of sublimation of ice from a frozen product also depends upon the dry cake resistance to the vapor transfer from the ice sublimation interface.

As used herein, the term "freeze-dryer" refers to a system comprises: (a) a lyophilization chamber with shelves where the filled vials are loaded for conducting lyophilization, (b) a condenser for capturing the sublimed water vapor as ice, (c) a refrigeration and a heating unit that facilitates temperature control, and (d) a vacuum pump that can reduce chamber pressure to subatmospheric values. Chamber pressure of the freeze-dryer is maintained at a setpoint by introducing an inert, dry bleed gas in a controlled manner (normally nitrogen gas). In most case, the lyophilization chamber is separated from the condenser via a main valve. The product vials are loaded to the shelves of the chamber with controlled shelf temperatures. (Chang et al.)

As used herein, the term "peptide" or "protein" includes any amino acid polymer having covalently linked amide bonds. Proteins comprise one or more amino acid polymer chains, generally known in the art as "peptide" or "polypeptides". A protein may contain one or multiple polypeptides to form a single functioning biomolecule. In some exemplary embodiments, the protein can be an antibody, a bispecific antibody, a multi-specific antibody, antibody fragment, monoclonal antibody, host-cell protein or combinations thereof.

In one aspect, the peptide or protein in the formulation of the present application is an antibody, an antibody fragment, a Fab region of an antibody, an antibody-drug conjugate, a fusion protein, a protein pharmaceutical product or a drug.

As used herein, the term "antibody" refers to immunoglobulin molecules consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has of a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL can be composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" is inclusive of, but not limited to, those that are prepared, expressed, created or isolated by recombinant means, such as antibodies isolated from a host cell transfected to express the antibody. An IgG comprises a subset of antibodies.

As used herein, the term "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a Fc fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins arc recombinant single chain polypeptide molecules in which immunoglobulin light and heavy chain variable regions are connected by a peptide linker. An antibody fragment may be produced by various means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex.

As used herein, the term "antibody-drug conjugate", or "ADC" can refer to antibody attached to biologically active drug(s) by linker(s) with labile bond(s). An ADC can comprise several molecules of a biologically active drug (or the payload) which can be covalently linked to side chains of amino acid residues of an antibody (Siler Panowski et al., Site-specific antibody drug conjugates for cancer therapy, 6 mAbs 34-45 (2013)). An antibody used for an ADC can be capable of binding with sufficient affinity for selective accumulation and durable retention at a target site. Most ADCs can have Kd values in the nanomolar range. The payload can have potency in the nanomolar/picomolar range and can be capable of reaching intracellular concentrations achievable following distribution of the ADC into target tissue. Finally, the linker that forms the connection between the payload and the antibody can be capable of being sufficiently stable in circulation to take advantage of the pharmacokinetic properties of the antibody moiety (e.g., long half-life) and to allow the payload to remain attached to the antibody as it distributes into tissues, yet should allow for efficient release of the biologically active drug once the ADC can be taken up into target cells. The linker can be: those that are non-cleavable during cellular processing and those that are cleavable once the ADC has reached the target site. With non-cleavable linkers, the biologically active drug released within the call includes the payload and all elements of the linker still attached to an amino acid residue of the antibody, typically a lysine or cysteine residue, following complete proteolytic degradation of the ADC within the lysosome. Cleavable linkers are those whose structure includes a site of cleavage between the payload and the amino acid attachment site on the antibody. Cleavage mechanisms can include hydrolysis of acid-labile bonds in acidic intracellular compartments, enzymatic cleavage of amide or ester bonds by an intracellular protease or esterase, and reductive cleavage of disulfide bonds by the reducing environment inside cells.

As used herein, the term "protein pharmaceutical product" includes an active ingredient which can be fully or partially biological in nature. In some exemplary embodiments, the protein pharmaceutical product can comprise a peptide, a protein, a fusion protein, an antibody, an antigen, vaccine, a peptide-drug conjugate, an antibody-drug conjugate, a protein-drug conjugate, cells, tissues, or combinations thereof. In some other exemplary embodiments, the protein pharmaceutical product can comprise a recombinant, engineered, modified, mutated, or truncated version of a peptide, a protein, a fusion protein, an antibody, an antigen, vaccine, a peptide-drug conjugate, an antibody-drug conjugate, a protein-drug conjugate, cells, tissues, or combinations thereof.

EXEMPLARY EMBODIMENTS

Embodiments disclosed herein provide compositions and methods for conducting lyophilization to obtain a target percentage of residual moisture of a lyophilized product which is stable for room temperature storage or has improved stability for refrigeration storage.

In some exemplary embodiments, this disclosure provides a lyophilized cake which has a target weight percentage of the at least one solvent molecule in the lyophilized cake, such as about 3-6%, about 4%, about 4.5%, about 2-5.5%, about 2.5-6%, about 3-4.5%, about 3.5-6.5%, about 4-5%, about 4.1%, about 4.2%, about 4.3%, about 4.4%, about 4.6%, about 4.7%, about 4.8% or about 4.9%.

In some exemplary embodiments, the shelf temperature of the freeze-dryer for conducting second drying can be the same as the shelf temperature of the freeze-dryer for conducting first drying (primary drying). In some aspects, the shelf temperature of the freeze-dryer for second drying (secondary drying) can be slightly higher than the shelf temperature of the freeze-dryer for first drying. In some aspects, the shelf temperature of the freeze-dryer for second drying can be lower than the shelf temperature of the freeze-dryer for first drying. In some aspects, the difference between the shelf temperature of the freeze-dryer for second drying and the shelf temperature of the freeze-dryer for first drying can be about 0-25° C., about 0-20° C., about 0-15° C., about 0-10° C., about 0-5° C., about 0-3° C., about 0-2° C., about 1° C., about 2° C., about 3° C., about 4° C., about 5° C., about 6° C., about 7° C., about 8° C., about 9° C. or about 10° C.

In some exemplary embodiments, the method of the present application further comprises determining an ending of the first drying (primary drying) based on a change of a PG pressure in the chamber of the freeze-dryer. In some aspects, the changes of pressures in the chamber of the freeze-dryer are measured by Pirani gauge and/or capacitance manometer. The differences between the measurements of Pirani gauge (PG) and capacitance manometer (CM), for example, PG-CM, are used as indicators to define the ending of the first drying or the ending of the secondary drying. In some aspects, the chamber pressure of the freeze-dryer can be maintained at a typical condition at about 100 mTorr or other typical condition, such as 50 or 200 mTorr.

In some exemplary embodiments, the formulation of the present application is subjected to lyophilization to obtain the lyophilized cake by placing the formulation in a chamber of a freeze-dryer. The formulation can be transferred to vials, such as glass vials, then the vials are placed in the chamber of the freeze-dryer. The fill depth of the vial is about 1 cm, about 1.5 cm, about 0.8 cm, about 0.9 cm, about 1.1 cm, about 1.2 cm, about 1.3 cm, about 1.4 cm, about 1.6 cm, about 1.7 cm, about 1.8 cm, about 1.9 cm or about 2 cm. The glass vial size is about 2 mL, about 5 mL, about 10 mL, about 20 mL, about 6 mL, about 7 mL, about 8 mL, about 9 mL, about 15 mL, about 25 mL, about 30 mL, about 40 mL or about 50 mL. The loading of the glass vials to the freeze-dryer can be full shelf load or partial shelf load.

In some exemplary embodiments, the formulation of the present application further comprises a buffer, an excipient, a stabilizer, a cryo-protectant, a lyo-protectant, a bulking agent, a plasticizer, or a combination thereof; wherein the stabilizer is polyol, sucrose, mannitol, trehalose, sorbital, amino acid, or a combination thereof; wherein the cryo-protectant or lyo-protectant is surfactant, sugar, salt, amino acid, or a combination thereof. In some aspects, the buffer comprises acetate or histidine hydrochloride, the buffer has a pH value of about 5.3, and the excipient is polysorbate 80. In some aspects, the stabilizer can be sucrose, wherein the ratio of sucrose to the peptide or protein is about 1:1, such as containing 50 mg/mL sucrose and 50 mg/mL protein. Some formulations comprises sucrose and protein at the ratio of about 1:1, about 3:1, about 10:1, or about from 1:1 to 10:1. In some aspects, the stabilizers include glycerol, mannitol, trehalose, sorbitol, sucrose, arginine hydrochloride, alanine, proline, glycine, sodium chloride, or a combination thereof. In some aspects, the stabilizer makes up from about 19.9% to about 82.2% of the weight of the lyophilized cake. In some aspects, the stabilizer is sucrose, and the stabilizer makes up from about 3% to about 15%, preferably about 5-11%, 4-7.5%, or 5-7.5% of the weight of the lyophilized cake, depending on the presence of other stabilizer components and the amount of protein, water, and other excipients. In an aspect, the ratio of protein to stabilizer by weight is between 1:1-3:1, preferably 1.2:1-2:1, more preferably about 1.5:1. In some aspects, the excipient comprises a surfactant, such as about 0.01% to about 0.96% surfactant. The surfactant may comprise a nonionic detergent, such as a fatty acylated polyethoxylated sorbitan. In some aspects, the pharmaceutically acceptable lyophilized cake is prepared from a pre-lyophilized aqueous solution, e.g., a protein formulation, which is prepared by combining a protein, a buffer, a nonionic surfactant, and one or more stabilizers in water. The solution is then freeze-dried to prepare a cake containing a desirable target residual moisture content.

It is understood that the method is not limited to any of the aforesaid lyophilization processes, formulations, freeze-dryer, methods of pressure measurements, pharmaceutical products, peptides, proteins or antibodies. The consecutive labeling of method steps as provided herein with numbers and/or letters is not meant to limit the method or any embodiments thereof to the particular indicated order.

Various publications, including patents, patent applications, published patent applications, accession numbers, technical articles and scholarly articles are cited throughout the specification. Each of these cited references is incorporated by reference herein in its entirety and for all purposes. Unless described otherwise, all technical and scientific terms used herein have the same meaning as commonly understood by one of ordinary skill in the art to which this invention belongs.

This disclosure will be more fully understood by reference to the following Examples, which are provided to describe this disclosure in greater detail. They are intended to illustrate and should not be construed as limiting the scope of this disclosure.

EXAMPLES

Methods

1. Determination of Residual Moisture

According to Patel et al., the percentages of residual moisture in samples during lyophilization were determined using gravimetric method or Karl Fisher method. Vials containing lyophilized samples were retrieved using a sample thief. If the selected sample vial had a complete melt-back after warming to room temperature due to the presence of residual ice, the residual moisture was calculated gravimetrically. If the selected sample vial retained the cake structure, the residual moisture was determined using Karl Fisher residual moisture analyzer. In some embodiments of the present application, in order to retrieve the vials containing lyophilized samples, the lyophilization run was stopped for retrieving the samples. Subsequently, the lyophilization run was restarted. In some embodiments of the present application, a Vapor Pro® moisture analyzer (Arizona Instrument LLC) was used to analyze the percentages of residual moisture in samples. A sample was heated in the Vapor Pro moisture analyzer and the evolved volatiles were passed to an analysis cell for the measurements of the moisture content of the flowing gas for converting into total water to calculate water percentages.

Example 1. Determining the Completion of Primary Drying

Previous studies were conducted to investigate the product stabilities of lyophilized protein formulations. The results indicated that the lyophilized products containing about 0% moisture content had relatively lower stabilities with the formation of higher amount of high molecular weight (HMW) aggregations. The lyophilized products containing about 3-5% moisture content had higher stabilities with lower amount of HMW aggregations. The target residual moisture content of the lyophilized product for achieving optimal stability under the storage condition at 25° C. was estimated to be about 4.0%, about 4.5% or about 3-5%.

Figure 4:
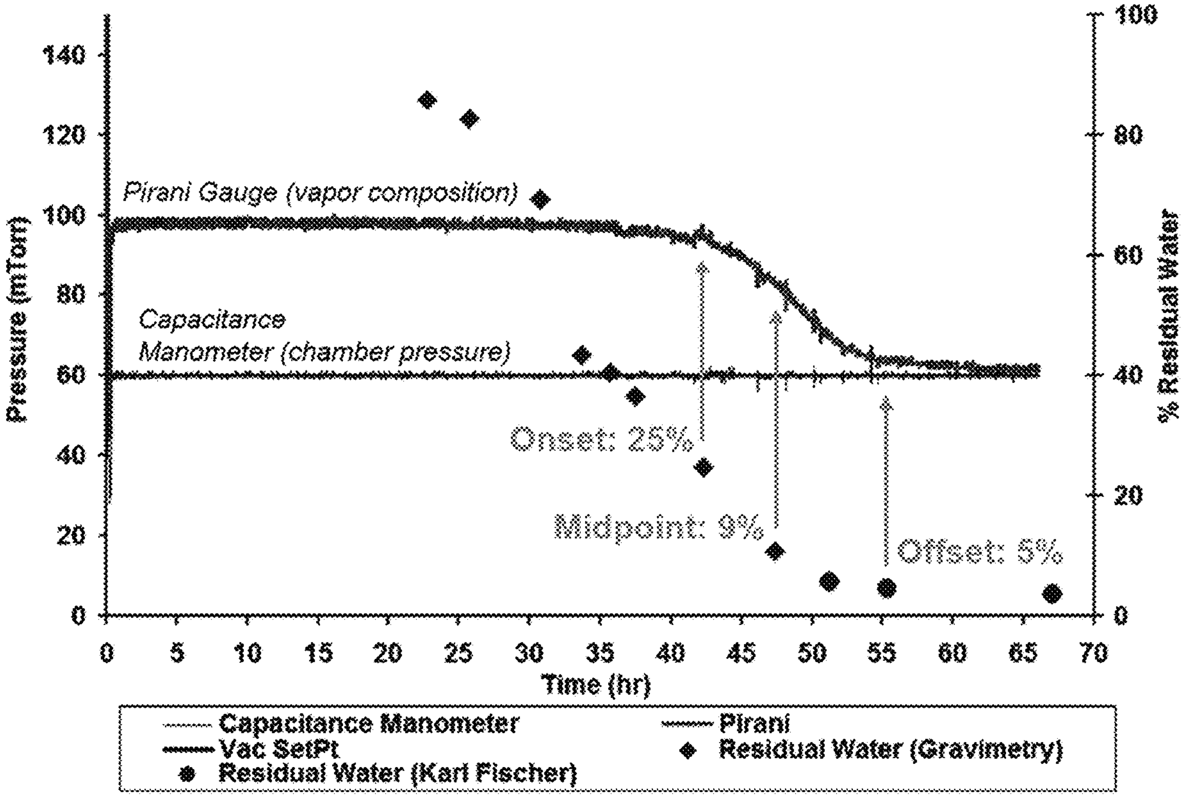
FIG. 4 shows the use of the differences between the measurements of the Pirani gauge (PG) and capacitance manometer (CM), for example, PG-CM, as indicators to define the apparent end point of primary drying, e.g., onset, midpoint and offset, which indicated the completion of ice sublimation in lyophilization processes according to Patel et al. and an exemplary embodiment. The measurements of PG-CM corresponding to relevant residual moisture percentages in the samples were indicated in the figure according to Patel et al. and an exemplary embodiment.
Figure 4:
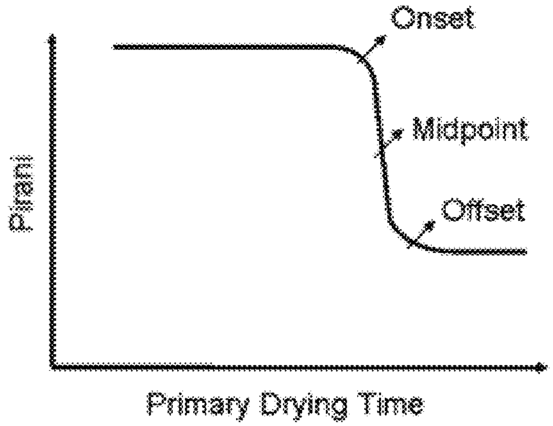

In order to reach the target residual moisture content of the lyophilized product at about 4.0%, about 4.5% or about 3-5% for achieving optimal stability under the storage condition at 25° C., the completion of primary drying, for example, sublimation, was determined during lyophilization processes. The apparent end point of primary drying, for example, onset, midpoint and offset, were determined by measurements of Pirani gauge at different time points of primary drying time as shown in FIG. 4 according to Patel et al. According to Patel et al., the profile of residual water percentages from the incomplete ice sublimation is relevant to chamber pressures which are measured by Pirani gauge and/or a capacitance manometer. The differences between the measurements of the Pirani gauge (PG) and capacitance manometer (CM), for example, PG-CM, were used as indicators to define global offset point which indicated the completion of sublimation (primary drying) in lyophilization processes. The experiments were conducted using protein formulations containing 5% sucrose or 5% mannitol. The measurements of PG-CM corresponding to the onset point had about 25% residual moisture in the sample as shown in FIG. 4. The measurements of PG-CM corresponding to the midpoint had about 9% residual moisture in the sample as shown in FIG. 4. The measurements of PG-CM corresponding to the offset point had about 5% residual moisture when ice sublimation fully complete in the sample as shown in FIG. 4. The protein formulation containing 5% sucrose had about 5% residual moisture at offset point. The protein formulation containing 5% mannitol had about 4% residual moisture at offset point.

Example 2. Develop Lyophilization Processes to Achieve Target Residual Moisture Contents In order to achieve target residual moisture content at about 3-5% of the lyophilized product, various experimental parameters of the lyophilization processes were tested. Various shelf temperatures of primary drying were tested, such as 0° C., −10° C., −20° C. or −30° C. Secondary drying (or extension of primary drying) was conducted after the completion of sublimation (e.g., primary drying). Several shelf temperatures of secondary drying, such as 0° C., −10° C., −20° C. or −30° C., were tested to investigate the changes of rate of desorption during secondary drying. The shelf temperature of secondary drying in the experimental designs of the present application was substantially lower than that of conventional secondary drying, since conventional secondary drying was commonly conducted at higher temperatures to reach less than about 1% or about 2% residual moisture content, such as about 40° C., about 35° C.-55° C. or about 25° C.-55° C. In contrast, in order to reach a slow rate of desorption, secondary drying of the present application was conducted at a temperature which was same as the shelf temperature of the primary drying, a temperature which was slightly higher than the shelf temperature of the primary drying or a temperature which was lower than the shelf temperature of the primary drying, as shown in FIG. 3.

The chamber pressure of the freeze-dryer was maintained at a typical condition at about 100 mTorr. Various protein formulations were tested including a protein formulation containing sucrose at the 1:1 ratio for protein to sucrose, such as containing 50 mg/mL protein and 50 mg/mL sucrose. The fill depth of the glass vial was about 1 cm, such as 2.5 mL fill in 5 mL glass vial. A controlled nucleation step was used during the freezing stage of the lyophilization process, since how a product freezes can impact its subsequent drying behavior and the final product quality attributes. Controlled nucleation can promote rapid rate of crystallization, such as formation of larger ice crystal. Large ice crystals can impose a lower resistance to water vapor flow from the ice sublimation interface to reduce the time required for primary drying. Additionally, controlling nucleation during freezing leads to less variability within a batch and between batches. Vials were removed at various time points for analysis including examining the appearance of cake, the moisture content and the glass transition temperature. Protein formulations containing MABB (a monoclonal antibody) were used for the lyophilization, such as a formulated drug substance comprising 50 mg/mL MABB, 10 mM acetate, 25 mM arginine hydrochloride, 0.2% polysorbate 80 and 5% sucrose at pH 5.3. The ratio of sucrose to protein was 1:1.

Figure 5:
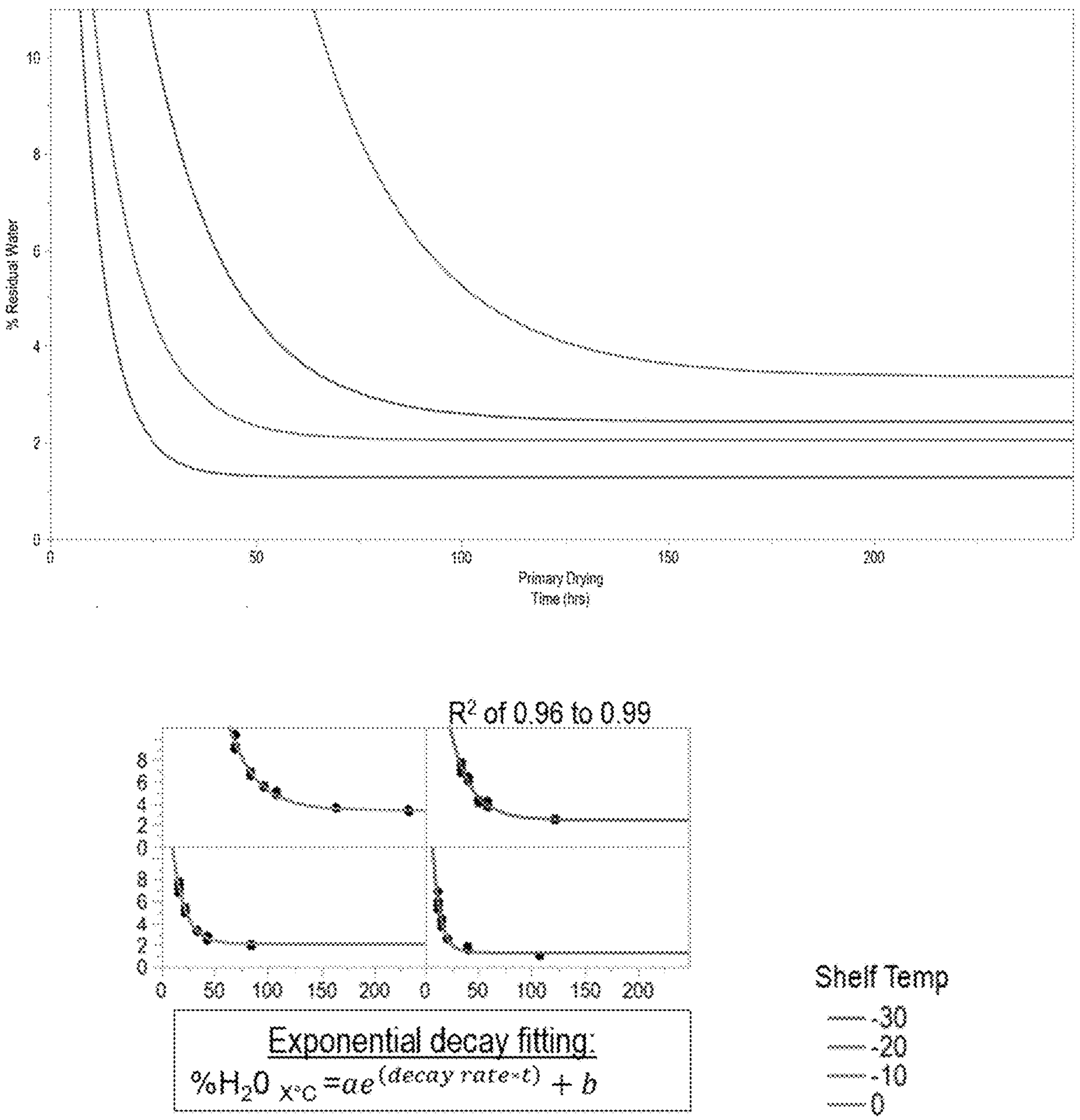
FIG. 5 shows rates of desorption after the completion of sublimation according to an exemplary embodiment. The secondary drying was conducted at same shelf temperature of the primary drying by extending the primary drying with the shelf temperatures of 0° C., −10° C., −20° C. or −30° C., according to an exemplary embodiment. In some aspects, there was no distinguished secondary drying.

The secondary drying was conducted at same shelf temperature of the primary drying by extending the primary drying. Shelf temperatures at 0° C., −10° C., −20° C. and −30° C. were tested. The rates of desorption after the completion of sublimation were analyzed by determining the percentages of residual water at different time points as shown in FIG. 5. The percentages of residual water in corresponding to different drying time points showed an exponential decay curve. The residual water content decreased at a rate proportional to its current rate initially with increased drying time. Eventually the decay reached a plateau approaching a constant value. When the shelf temperature was maintained at −30° C., the decay of the residual water content reached a plateau close to 3.5% which was within the range of the target weight percentage of residual moisture at 3-5% as shown in FIG. 5. Since the end value was within the range of the target percentage, the drying time can be extended without further reduction of the moisture content for shelf temperature of −30° C.

As shown in FIG. 5, when the shelf temperature was maintained at −20° C., the decay of the residual water content reached a plateau close to 2.5% which was outside the range of the target weight percentage of residual moisture at 3-5%. When the shelf temperature was maintained at −10° C., the decay of the residual water content reached a plateau close to 2.1%, which was outside the range of the target weight percentage of residual moisture at 3-5%. When the shelf temperature was maintained at 0° C., the decay of the residual water content reached a plateau close to 1.2%, which was outside the range of the target weight percentage of residual moisture at 3-5%. Therefore, for the shelf temperatures which were higher, such as −20° C., −10° C. or 0° C., the drying time needed to be controlled in order to reach the target weight percentage of residual moisture at 3-5%. The drying time to achieve a target moisture content in the lyophilized product at a given shelf temperature can be calculated by the exponential decay equation knowing the desorption rate at the shelf temperature. When the shelf temperature was relatively higher, the drying time after the completion of sublimation was relatively shorter to sufficiently reduce moisture content to target percentage by controlling rate of desorption.

Example 3. Product Glass Transition Temperature

Figure 6:
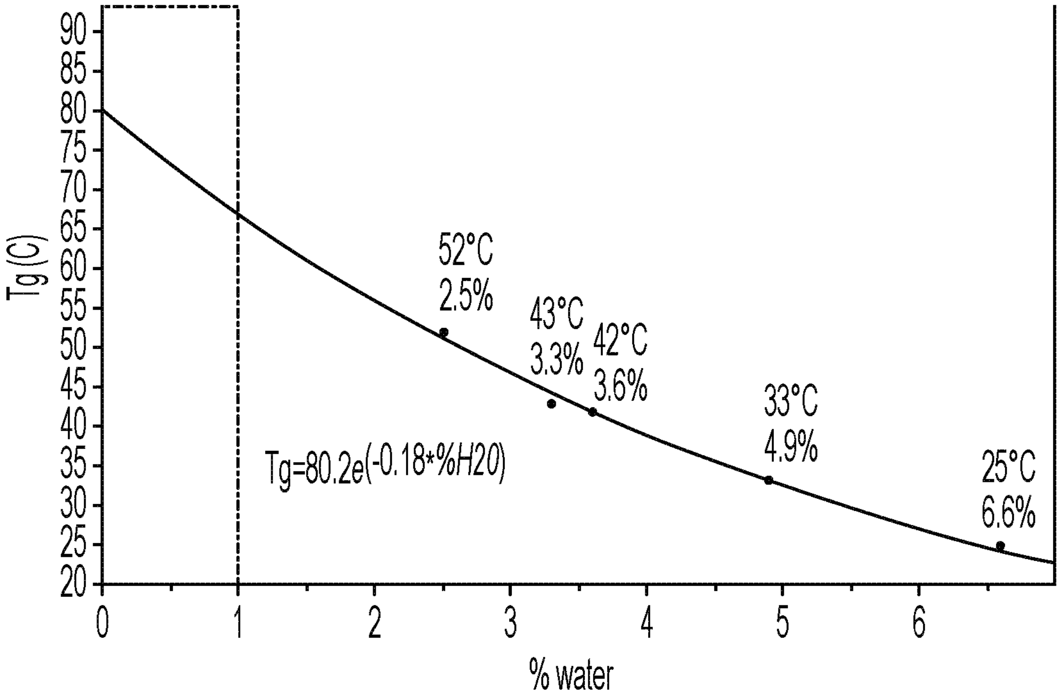
FIG. 6 shows glass transition temperatures of the lyophilized protein formulations corresponding to the percentages of residual moisture contents including the recommended storage temperatures according to an exemplary embodiment.

Glass transition temperatures (Tg) of the lyophilized protein formulations in corresponding to the percentages of residual moistures were analyzed. Protein formulations contained 50 mg/mL MABB (a monoclonal antibody), 5% sucrose, 25 mM arginine hydrochloride, 10 mM acetate and 0.2% polysorbate 80 at pH 5.3 were lyophilized. As shown in FIG. 6, Tg decreased significantly, when the percentages of residual moistures increased. The recommended storage temperature was below 52° C. for 2.5% residual moisture, 43° C. for 3.3% residual moisture, 42° C. for 3.6% residual moisture, 33° C. for 4.9% residual moisture and 25° C. for 6.6% residual moisture. For a room temperature storage product, the moisture content of this formulation was preferably not above 5%.

Example 4. Appearance of the Lyophilized Cake

Various lyophilization cycles were tested to examine the appearance of the lyophilized cakes. It is desirable that the cake has no sign of collapse or melt-back during freeze-drying. Melt-back of the cake can be due to the eutectic melting of crystalline agents in product formulation at the ice sublimation interface during primary drying. Melt-back of the cake can be considered as a form of partial or complete cake collapse caused by incomplete ice sublimation during primary drying. A desirable cake has mostly uniform appearance with some minor flaking or crumbling along the surfaces or edges.

Six different cycles of lyophilization were tested using the shelf temperatures of primary drying at −20° C. or −30° C. as shown in Table 1. Protein formulations containing MABB (a monoclonal antibody) were used for the lyophilization using a formulated drug substance comprising 50 mg/mL MABB, 10 mM acetate, 25 mM arginine hydrochloride, 0.2% polysorbate 80 and 5% sucrose at pH 5.3. The ratio of sucrose to protein was 1:1.

TABLE 1

| Primary drying conditions | | | | |
|---|---|---|---|---|
| Cycle No. | Controlled Nucleation at −5° C. | Ts (Shelf Temp, ° C.) | Chamber Pressure = CM (mTorr) | Absolute difference (PG-CM) at ~approx end of cycle (mTorr) |
| 1 | Yes | −20 | 100 | 40 |
| 2 | Yes | −20 | 100 | 5 |
| 3 | Yes | −30 | 100 | 5 |
| 4 | Yes | −20 | 100 | 1 |
| 5 | Yes | −30 | 100 | 0 |
| 6 | Yes | −30 | 100 | 15 |

The chamber pressure of the freeze-dryer was maintained at a typical condition at about 100 mTorr. A controlled nucleation step at −5° C. was used during the freezing stage of the lyophilization process. Chamber pressures of the freeze-dryer were measured by Pirani gauge and a capacitance manometer. The differences between the measurements of the Pirani gauge (PG) and capacitance manometer (CM), for example, PG-CM, were used as indicators to define global end point of the completion of sublimation (primary drying) in lyophilization processes.

When the desirable absolute pressure difference, for example, PG-CM, was met, the lyophilization processes for the primary drying were completed. The tested results are shown in Table 2. The cakes of cycles 1 and 6 showed the form of melt-back which indicated the presence of ice due to the incompletion of the sublimation, when the difference (PG-CM) is large (15 mTorr or above). The cakes of cycles 2-5 showed the appearance of good cakes, for example, not having collapse, discoloring and melt-back, indicating the completion of ice sublimation when the difference (PG-CM) is small (5 mTorr or below). After the completion of sublimation, the percentage of the residual moisture content of the lyophilization products were used to model the rate of desorption curves.

TABLE 2

| Testing absolute pressure difference | | | |
|---|---|---|---|
| Cycle No. | Ts (Shelf Temp, ° C.) | PG-CM (mTorr) | Lyophilized Cake Appearance |
| 1 | −20 | 40 | Melt-back |
| 2 | −20 | 5 | Good Cake |
| 3 | −30 | 5 | Good Cake |
| 4 | −20 | 1 | Good Cake |
| 5 | −30 | 0 | Good Cake |
| 6 | −30 | 15 | Melt-back |

Example 5. Lyophilization Processes With Longer Duration Time

Lyophilization cycles with longer duration time and larger number of vials were tested using the shelf temperatures at −20° C. Protein formulations containing MABB (a monoclonal antibody) were used for the lyophilization using a formulated drug substance comprising 50 mg/mL MABB, 10 mM acetate, 25 mM arginine hydrochloride, 0.2% polysorbate 80 and 5% sucrose at pH 5.3. The ratio of sucrose to protein was 1:1. The fill depth of the glass vial was about 1 cm, such as 2.5 mL fill in 5 mL glass vial. Twenty-seven vials were tested. The chamber pressure of the freeze-dryer was maintained at a typical condition at about 100 mTorr.

Figure 7:
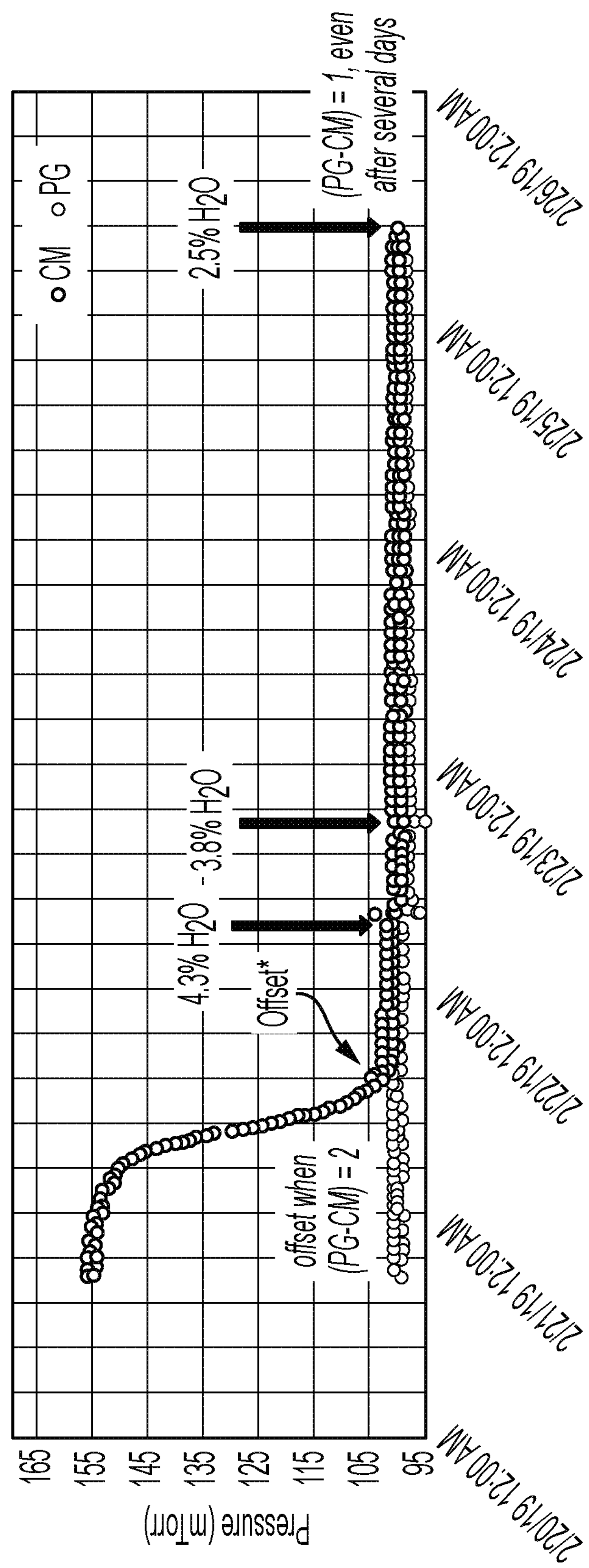
FIG. 7 shows measurements of chamber pressures in lyophilization processes with extended duration time as measured by a capacitance manometer (CM) and Pirani gauge (PG) according to an exemplary embodiment. The chamber pressures were plotted against drying time according to an exemplary embodiment. The difference between PG and CM, for example, (PG-CM), was used to determine the offset point of the primary drying according to an exemplary embodiment.

The end point of the primary drying (sublimation) was dependent on load. As shown in FIG. 7, the end of sublimation occurred with the PG pressure curve showing an offset transition, when the value of (PG-CM) reached 2, for example, the completion of primary drying. The residual moisture content gradually decreased after the completion of sublimation to reach the target weight percentage of residual moisture at 3-5%, such as reduced to 4.3% or 3.8% as indicated in FIG. 7. When the lyophilization process continued for longer duration, the residual moisture content did not reduce significantly which was still within the acceptable range of 3-5%. When the duration time of the lyophilization was extended to several day, the residual moisture content reached 2.5%.

Figure 8:
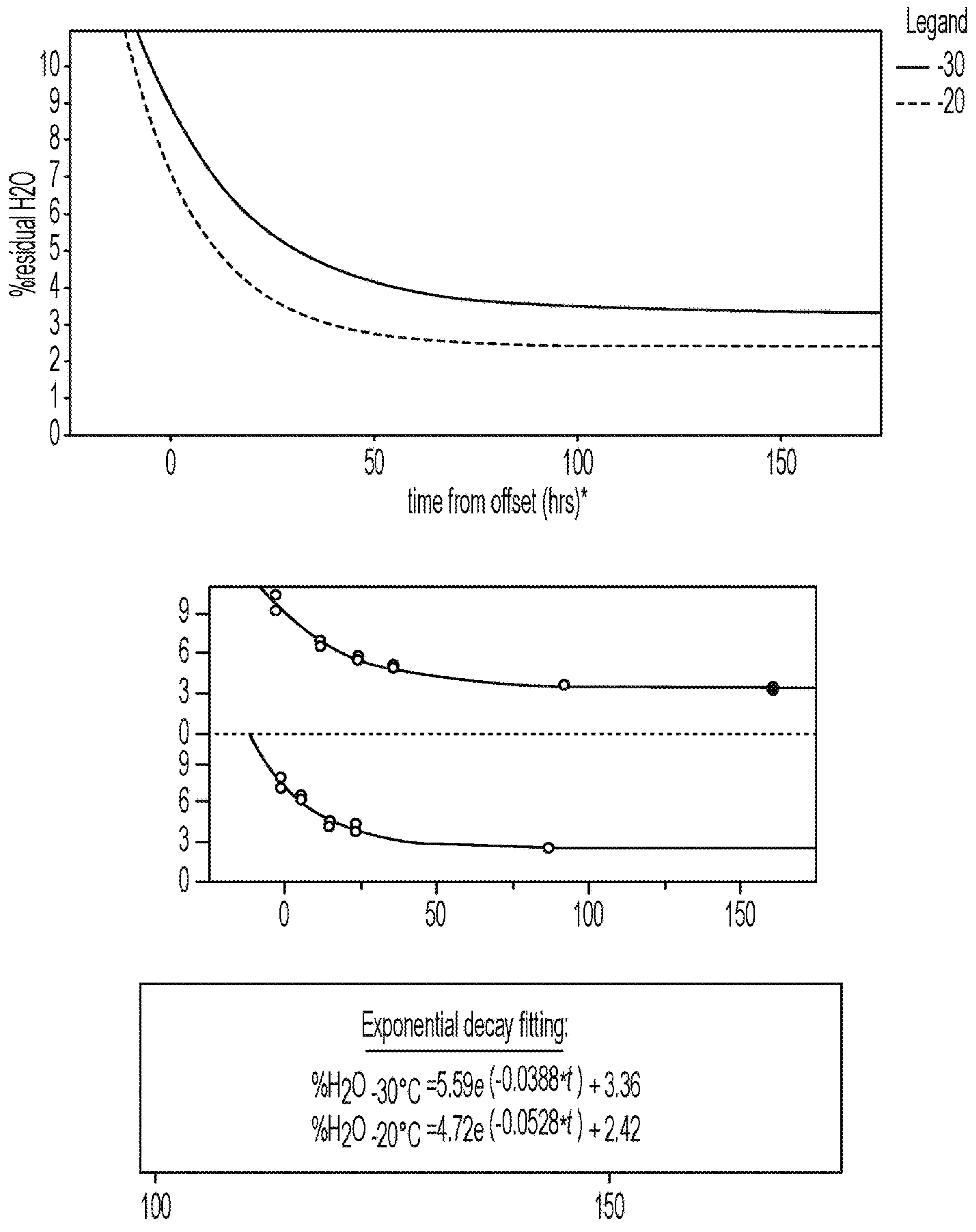
FIG. 8 shows rates of desorption after completion of ice sublimation for shelf temperature of −20° C. or −30° C. with extended duration time of primary drying according to an exemplary embodiment. The obtained moisture contents were plotted against the duration time from offset according to an exemplary embodiment.

The rates of desorption after completion of sublimation were analyzed using shelf temperature of −20° C. or −30° C. As shown in FIG. 8, the moisture content (Y axis) reached 9% after completion of sublimation (primary drying) for shelf temperature of −30° C. The secondary drying (desorption) (or extended primary drying) was conducted by controlling rate of desorption at shelf temperature of −30° C. with extended duration time, such as 50 hr, 100 hr, 150 hr or longer as indicated in X axis of FIG. 8, for example, time from offset point of PG pressure curve (end of ice sublimation). The obtained residual moisture contents were within the range of target weight percentage of residual moisture at 3-5% for shelf temperature of −30° C. for extended duration time from about 30 hr up to 150 hr or longer. As shown in FIG. 8, the moisture content reached 7% after completion of sublimation (primary drying) for shelf temperature of −20° C. The secondary drying (desorption) was conducted by controlling rate of desorption at shelf temperature of −20° C. with extended duration time, such as 50 hr, 100 hr, 150 hr or longer as indicated in X axis of FIG. 8, for example, time from offset point of PG pressure curve (end of ice sublimation). The obtained residual moisture contents were within the range of target weight percentage of residual moisture at 3-5% for shelf temperature of −20° C. within 50 hr duration time. The obtained residual moisture contents were slightly below the target percentage of residual moisture content for extended duration time up to 150 hr or longer for shelf temperature of −20° C. indicating the desorption time should be controlled within 50 hrs at −20° C. shelf temperature preferably between 10 to 30 hours.

The design of experiments (DOE) for developing lyophilization was conducted as shown in Table 3. The protein concentrations were tested at 5-15%. Sucrose concentrations were tested at 0-5%. The arginine hydrochloride concentrations were tested at 0-2%.

TABLE 3

| Design of experiment (DOE) | | | | |
|---|---|---|---|---|
| % Protein | Buffer | % Sucrose | % Arginine HCL | Comments |
| 5% (50 mg/mL) | X mM of Y buffer | 0 | 0 | Just protein and buffer |
| 5% (50 mg/mL) | X mM of Y buffer | 5 | 0 | |
| 5% (50 mg/mL) | X mM of Y buffer | 0 | 2 | |
| 5% (50 mg/mL) | X mM of Y buffer | 5 | 2 | |
| 10% (100 mg/mL) | X mM of Y buffer | 2.5 | 1 | DOE midpoint |
| 15% (150 mg/mL) | X mM of Y buffer | 0 | 0 | Just protein and buffer |
| 15% (150 mg/mL) | X mM of Y buffer | 5 | 0 | |
| 15% (150 mg/mL) | X mM of Y buffer | 0 | 2 | |
| 15% (150 mg/mL) | X mM of Y buffer | 5 | 2 | |

What is claimed is:

1. A method for producing a lyophilized drug product, comprising:
- obtaining a formulation comprising a formulated drug substance; and
- subjecting the formulation to lyophilization to produce a lyophilized drug product, wherein the lyophilization comprises a first drying step and a secondary drying step, wherein the secondary drying step is conducted at a temperature below about 0° C., and the lyophilized drug product comprises a moisture content from about 3% to about 5%.

2. The method of claim 1, wherein the formulated drug substance comprises an antibody, an antibody fragment, a Fab region of an antibody, an antibody-drug conjugate, or a fusion protein.

3. The method of claim 1, wherein the moisture content is from 4% to 4.5%.

4. The method of claim 1, wherein the lyophilized drug product has improved stability when stored at about 20-25° C.

5. The method of claim 1, wherein the method further comprises determining an ending of the first drying step based on a change of a pressure in the chamber of the freeze-dryer.

6. The method of claim 1, wherein the temperature of the secondary drying step is not above the about the temperature of the first drying step.

7. The method of claim 1, wherein a temperature of the secondary drying step is from about 0° C. to about −30° C.

8. The method of claim 1, wherein a temperature of the secondary drying step is about −10° C. to about −30° C.

9. The method of claim 1, wherein a duration of the secondary drying step is about 10 to about 150 hours.

10. The method of claim 1, wherein the formulation further comprises at least one buffer, at least one excipient, at least one stabilizer, at least one cryo-protectant, at least one bulking agent, at least one plasticizer, or a combination thereof.

11. The method of claim 10, wherein the at least one buffer comprises acetate and/or histidine hydrochloride.

12. The method of claim 10, wherein the at least one buffer has a pH value of about 5.3 to about 6.

13. The method of claim 10, wherein the at least one excipient comprises polysorbate 80.

14. The method of claim 10, wherein the at least one stabilizer comprises sucrose.

15. The method of claim 10, wherein the at least one stabilizer comprises a polyol, sucrose, mannitol, trehalose, sorbitol, an amino acid, or a combination thereof.

16. The method of claim 10, wherein the at least one cryo-protectant comprises a surfactant, sugar, salt, an amino acid, or a combination thereof.

17. The method of claim 10, wherein the formulation comprises:

a. sucrose at a concentration of above 0% to about 5%;
b. arginine at a concentration of above 0% to about 2%;
c. acetate at a concentration of above 0 mM to about 10 mM;
d. histidine; and/or
e. polysorbate 80 at a concentration of above 0% to about 0.2%.

18. The method according to claim 1, wherein the lyophilized drug product has improved stability when stored at about 2 to 8° C.

19. The method according to claim 6, wherein the temperature of the secondary drying step is lower than the temperature of the first drying step.

* * * * *